United States Patent

Baur et al.

[11] Patent Number: 5,955,045
[45] Date of Patent: Sep. 21, 1999

[54] REMOVAL OF NITROGEN OXIDES FROM GASES

[75] Inventors: Karl Baur, Baierbrunn; Hans-Peter Langebach, Grunwald; Hartmut Neumann, München; Ulrike Wenning, Karlsfeld, all of Germany

[73] Assignee: Linde Aktiengesellschaft, Wiesbaden, Germany

[21] Appl. No.: 08/874,662

[22] Filed: Jun. 13, 1997

[30] Foreign Application Priority Data

Jun. 14, 1996 [DE] Germany .......................... 196 23 791

[51] Int. Cl.$^6$ ........................... B01D 53/02; B01D 53/56
[52] U.S. Cl. .................................... 423/239.1; 208/254 R; 585/824
[58] Field of Search ................ 423/235, 239.1; 502/20, 56; 585/810, 820, 826, 827, 824; 208/106–124, 254 R

[56] References Cited

U.S. PATENT DOCUMENTS 3,840,642 10/1974 Negra et al. .......................... 423/213.7
4,692,318  9/1987 Tolpin et al. ........................ 423/215.5

FOREIGN PATENT DOCUMENTS 614692  9/1994 European Pat. Off. .

*Primary Examiner*—Michael Lewis
*Assistant Examiner*—Peter DiMauro
*Attorney, Agent, or Firm*—Millen, White, Zelane & Branigan, P.C.

[57] ABSTRACT

For selectively removing nitrogen oxides from a carrier gas that contains hydrocarbons, the nitrogen oxides are removed by chemisorption on metal oxides, without the occurrence of undesirable secondary reactions. The metal oxides are preferably formed from metals of the 6th to 8th subgroups, whereby manganese dioxide ($MnO_2$,) is especially preferred as a metal oxide. The process can be conducted with one or more reactor beds, which preferably operate at 10 to 40° C. and are regenerated with nitrogen at a temperature of 130 to 170° C.

By removing nitrogen oxides from an olefin-rich gas, for example from the waste gas of an FCC unit, the resultant gas can then be fed to a cryogenic olefin extraction stage without danger of explosion.

Such a waste gas contains unsaturated hydrocarbons, hydrogen, carbon monoxide, and oxygen, the oxygen having a concentration preferably between 100 and 5000 mol ppm.

20 Claims, No Drawings

REMOVAL OF NITROGEN OXIDES FROM GASES

FIELD OF THE INVENTION

This invention relates to a process for selectively removing nitrogen oxides from a carrier gas that contains hydrocarbons.

BACKGROUND OF THE INVENTION

The need to remove nitrogen oxides from such gases exists, for example, in the case of an ethylene unit designed to process olefins from an FCC (Fluidized Catalytic Cracking) unit. In the FCC unit, the carbon to carbon bonds of long-chain hydrocarbons are cleared, so as to produce the desired light olefins. When regeneration of the FCC catalyst is conducted with air, there are produced nitrogen oxides, such as NO and $NO_2$. In addition, free oxygen is present. Especially at low temperatures of below 0° C., such as occur in, for example, the low-temperature portion of an ethylene unit, NO reacts with the oxygen that is always present at least in traces so as to form $N_2O_3$ having a boiling point of –102° C. and into $N_2O_4$ having a boiling point at –11° C. These nitrogen oxides can react with olefinic hydrogens having conjugated double bonds, for example with butadiene, with the formation of explosive resins which accumulate in the low-temperature separation of the olefin unit. These problems are described in detail in the publication: H. Bauer, Noncryogenic and Safe Demethanization of FCC Off Gases, *Linde Reports on Science and Technology*, 55, (1995), pages 15–18.

In addition, the formation of NO in an FCC unit cannot be avoided at an economically reasonable cost. Previously known are non-cryogenic processes for extracting olefinic hydrocarbons by absorption in scrubbing agents; such processes, however, require expensive analytical and operational procedures to avoid the build-up of explosive resins, whereby an additional necessary investment in apparatus increases the cost of the process. Conversely, heretofore a process for selectively separating nitrogen oxides from FCC residual gases was unknown.

SUMMARY OF THE INVENTION

An object of the invention is therefore to selectively remove nitrogen oxides from gas that contains hydrocarbon, for example, from FCC waste gas. Another object is to be able to provide cryogenic processes for olefin extraction after the nitrogen oxides are removed.

Upon further study of the specification and appended claims, further objects and advantages of this invention will become apparent to those skilled in the art.

The objects are achieved according to the invention by a process in which the nitrogen oxides are removed by chemisorption on metal oxides.

In principal, the removal of nitrogen oxides from gases is known in the art. In the publication Hamid Arastoopour and Hossein Hariri, $NO_x$ Removal with High-Capacity Metal Oxides in the Presence of Oxygen, Ind. Eng. Chem. Process Des. Dev. 1981, 20, pages 223–228, a process is described for purifying flue gases. Gases with a high oxygen content of 3% and a high nitrogen monoxide concentration of 680 mol ppm in the presence of water vapor with manganese dioxide as a sorbent are studied, and under these conditions a relatively low level of sorption is achieved. The sorbent is regenerated thermally at 500° C. The chemisorption of nitrogen monoxide on manganese dioxide is attributed to the following chemical reaction equation:

$$MnO_2 + 2NO + O_2 \leftrightarrow Mn(NO_3)_2$$

with equilibrium at high temperatures being shifted to the left-hand side of the equation, thereby making thermal regeneration possible.

In addition to the reaction that is mentioned in Arastoopour, the following chemical reaction of the manganese dioxide with nitrogen dioxide is also possible:

$$MnO_2 + 2NO_2 \leftrightarrow Mn(NO_3)_2$$

According to DE 3520024, laid open Dec. 4, 1986, $MnO_2$ is a catalyst for reduction processes as well.

One skilled in the art previously did not consider testing a gas that contains hydrocarbons, especially olefins, together with hydrogen, in a reactor with $MnO_2$ since the catalytic action of $MnO_2$ would make it likely that the unsaturated hydrocarbons would be hydrogenated. Also, the heat of reaction of trace components, such as carbon monoxide for example, reacting with oxygen to form carbon dioxide, can result in uncontrollable and undesirable reactions. Laboratory tests with catalyst T 2525 from the Sudchemie dchemie Company, which consists of $MnO_2$ on aluminum oxide, and with other $MnO_2$-containing catalysts with another carrier, e.g., silicon dioxide, lead to the surprising result that traces of NO are adsorbed at high yields without the expected undesirable secondary chemical reactions, i.e., without CO being oxidized to CO2, or hydrocarbon to $H_2O$ and $CO_2$.

The carrier gas preferably also contains traces of oxygen, especially between 1000 and 5000 mol ppm, since oxygen promotes the chemisorption of nitrogen oxides. Surprisingly, 0.3 mol % of oxygen does not lead to any secondary reactions. This is unexpected since $MnO_2$ is known to one skilled in the art as a catalyst for hydrocarbon oxidation, even at temperatures below 100° C.

The removal of nitrogen oxides from an olefin-rich refinery waste gas represents an especially preferred use. This use is advantageous when, for example, nitrogen is removed from FCC off-gases from a refinery since these gases have a high proportion of valuable hydrocarbon products. Representative FCC off-gases have the following composition

| | |
|---|---|
| Saturated hydrocarbon (C1-C3) | 45–65 mol % |
| Unsaturated hydrocarbon (C2-C3) | 15–25 mol % |
| Higher hydrocarbon | 1–10 mol % |
| $H_2$ | 15–20 mol % |
| $N_2$ | 5–10 mol % |
| CO | 0–2 mol % |
| $O_2$ | 500–2000 mol ppm |
| $H_2S$ | 20–100 mol ppm |
| $NH_3$ | 5–20 mol ppm |
| $AsH_3$ | 0.01–0.5 mol ppm |
| $NO_x$ | <5 mol ppm |

Traces of $CO_2$, COS, $SO_x$, HCN, Mercaptans, Chloride

In the process according to the invention, metal oxides, especially orders of metals of the 6th to 8th subgroups of the periodic system which can form a nitrate, e.g., Mn, Cr, Co and Ni, particularly commercial catalysts, can be advantageously used. Of these, $MnO_2$ has proved to be the most efficient; thus, the catalysts preferably contain manganese dioxide or a support, for example, in granular form that is coated with manganese dioxide. In the reactor bed that is traversed by the process gas, chemisorption of the nitrogen oxides on $MnO_2$ occurs, which in this case forms $Mn(NO_3)_2$. The reactor bed must therefore be regenerated before breakthrough of the nitrogen oxides. For this purpose, the reactor bed is advantageously flushed with an inert warm gas, preferably nitrogen, at a temperature of 100 to 300° C., preferably 130 to 170° C. Crushed catalyst particles, leading to a higher specific surface, permit longer on stream times before regeneration.

For the chemisorption step, an operating temperature of between 5 and 100° C. is advantageous, with a temperature of between 10 and 40° C. being especially advantageous. The preferred pressure is between 1 and 50 bar. The preferred space velocity is between 300 and 12,000 $h^{-1}$, with the especially preferred velocity being between 500 and 8,000 $h^{-1}$.

The particular apparatus for removing nitrogen oxides from gases depends on the boundary conditions of the application. To remove traces of nitrogen oxides on the order of below 0.1 mol ppm, or if nitrogen oxides occur in the carrier gas only sporadically or if correspondingly long breaks in operation so allow, a single reactor bed can advantageously be used.

If continuous operation is necessary, at least two interchangeable reactor beds are advantageously used. At least one reactor bed provides the function of chemisorption while the reactor bed or other reactor beds are being regenerated. Before breakthrough, the reactor beds are switched so that continuous removal of nitrogen oxides is made possible.

It is contemplated that the present invention is applicable to all hydrocarbon gases for the elimination of $NO_x$ even when the $NO_x$ is present in a concentration of less than 1 mol ppm, in view of the high selectivity of $MnO_2$ for the chemisorption of $NO_x$.

Without further elaboration, it is believed that one skilled in the art using the preceding description, can utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are mol fractions.

EXAMPLE 1

Utilizing a catalyst from the Südchemie Company, Type 2525 $MnO_2$ on $Al_2O_3$, laboratory tests were conducted at room temperature and atmospheric pressure on the following gas:

| | |
|---|---|
| Space velocity | 4000 $h^{-1}$ |
| NO content | 20 mol ppb |
| $O_2$ content | 520 mol ppm |
| saturated $C_1$–$C_3$ hydrocarbons | about 70 mol % |
| $H_2$ | 25 mol % |
| CO | 2 mol % |
| remainder | $N_2$ |

An NO removal rate of 85% was achieved even after an operating time of more than 130 hours.

EXAMPLE 2

Similar tests with ethylene and propylene instead of saturated hydrocarbons result in the same NO removal rate as in Example 1. No secondary reactions owing to oxidation of carbon monoxide and hydrocarbons or hydrogenation of olefins were noted.

All tests for adsorption of nitrogen oxides were carried out at atmospheric pressure and at a space velocity of about 4000 $h^{-1}$. The use of higher pressures would probably improve the removal of nitrogen oxides.

For the details of downstream cryogenic separations of NO-depleted hydrocarbon streams, see the aforementioned references as well as Netzer, D., "Economically recover olefins from FCC off-gases,"*Hydrocarbon Processing*, April 1997, and the literature and bibliography cited therein, and in particular to the flowsheet of FIG. 2 and the description thereof on pages 16 and 17 of Bauer, *Linde Reports on Science and Technology*, 55, (1995), pages 15–18.

The preceding examples can be repeated with similar success by substituting the generically or specifically described reactants and/or operating conditions of this invention for those used in the preceding examples.

The entire disclosure of all applications, patents and publications, cited above, and of corresponding German No. 196 23 791.2, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for selectively removing a nitrogen oxide from a hydrocarbon-containing carrier gas optionally containing at least one of olefins and CO, said process comprising contacting said carrier gas with a metal oxide at a temperature between 0 and 100° C., said metal oxide being capable of removing nitrogen oxide by chemisorption, and removing the nitrogen oxide by chemisorption on the metal oxide to convert the nitrogen oxide to a compound of said metal and substantially without undesirable secondary reactions of olefins being hydrogenated or of CO being oxidized to $CO_2$ or hydrocarbons to $H_2O$ and CO.

2. A process according to claim 1, wherein the carrier gas contains unsaturated hydrocarbons, hydrogen and carbon monoxide.

3. A process according to claim 1, wherein the carrier gas also contains oxygen.

4. A process according to claim 3, wherein the oxygen is present in a concentration between 100 and 5000 mol ppm.

5. A process according to claim 1, wherein the metal oxide is formed from a metal of the 6th to 8th subgroups, of the Periodic Table of the Elements.

6. A process according to claim 1, wherein the metal oxide is manganese dioxide thereby forming $Mn(NO_3)_2$.

7. A process according to claim 6, wherein the manganese dioxide is supported by aluminum oxide or silicon dioxide.

8. A process according to claim 1, wherein the removal of nitrogen oxide is performed at a temperature of between 0 and 900° C.

9. A process according to claim 1, conducted at a temperature between 10 and 40° C.

10. A process according to claim 9, conducted at a pressure between 1 and 50 bar.

11. A process according to claim 1, wherein the removal of nitrogen oxide is performed at a space velocity of between 300 and 12000 $h^{-1}$.

12. A process according to claim 10, where the removal of nitrogen oxide is conducted at a space velocity between 500 and 8000$h^{-1}$.

13. A process according to claim 1 conducted in at least one reactor bed containing manganese dioxide or a support coated with manganese dioxide and wherein the reactor bed accomplishes the chemisorption of the nitrogen oxides and, periodically is regenerated, wherein the reactor bed that is to be regenerated is flushed by a non-reactive gas having a temperature of approximately 100 to 300° C.

14. A process according to claim 13, wherein the non-reactive gas is nitrogen at 130–170° C.

15. A process according to claim 13, wherein only one reactor bed is used when nitrogen oxides are present in traces of less than 0.1 mol ppm.

16. A process according to claim 13, wherein at least two reactor beds are connected so that continuous operation of the removal of nitrogen oxides is achieved, by the reactor beds alternately assuming the task of chemisorption of nitrogen oxides, while other reactor bed(s) are regenerated.

17. A process according to claim 1, wherein the carrier gas is an olefin-rich gas produced by a thermal or catalytic cracking process.

18. A process according to claim 16, wherein said gas originates from an FCC unit of a refinery and has the following composition

| | |
|---|---|
| Saturated hydrocarbon (C1-C3) | 45–65 mol % |
| Unsaturated hydrocarbon (C2-C3) | 15–25 mol % |
| Higher hydrocarbon | 1–10 mol % |
| $H_2$ | 15–20 mol % |
| $N_2$ | 5–10 mol % |
| CO | 0–2 mol % |
| $O_2$ | 500–2000 mol ppm |
| $H_2S$ | 20–100 mol ppm |
| $NH_3$ | 5–20 mol ppm |
| $AsH_3$ | 0.01–0.5 mol ppm |
| $NO_x$ | <5 mol ppm |

Traces of $CO_2$, COS, $SO_x$, HCN, Mercaptans, Chloride.

19. A process according to claim 1, said carrier gas being olefin-rich and further comprising passing the olefin-rich gas to a cryogenic olefin extraction stage ater the ntirogen oxide is selectively removed.

20. A process according to claim 2, wherein the carrier gas also contains oxygen.

* * * * *